United States Patent [19]

DiLeo et al.

[11] Patent Number: 5,120,901
[45] Date of Patent: Jun. 9, 1992

[54] OLEFIN PURIFICATION PROCESS

[75] Inventors: Thomas J. DiLeo, Baton Rouge, La.; Cynthia W. Hermann, Houston, Tex.; Carroll W. Lanier, Baton Rouge, La.; Joachim W. Wolfram, Houston, Tex.

[73] Assignee: Ethyl Corporation, Richmond, Va.

[21] Appl. No.: 722,320

[22] Filed: Jun. 27, 1991

[51] Int. Cl.$^5$ .......................... C07C 7/00; C07C 2/02; C07C 2/24
[52] U.S. Cl. .................... 585/851; 585/833; 585/868; 585/521; 585/525; 585/527; 585/514
[58] Field of Search ............... 585/514, 521, 525, 527, 585/851, 833, 868

[56] References Cited

U.S. PATENT DOCUMENTS 3,367,987  2/1968  Walsh .................................. 585/851
3,742,082  6/1973  Brennan ............................. 585/510
3,907,922  9/1975  Heilman et al. .................... 585/510

Primary Examiner—Anthony McFarlane
Assistant Examiner—Nhat Phan
Attorney, Agent, or Firm—David M. Bunnell

[57] ABSTRACT

A process for removing vinylidene olefin from an olefin mixture containing about 1 to 55 mole percent vinylidene olefin, 0 to 20 mole percent internal olefin and the balance vinyl olefin, said process comprising:
(a) reacting said olefin mixture in the presence of a $BF_3$/phosphorus acid catalyst system so as to selectively dimerize vinylidene olefins, and
(b) separating said vinyl olefin and internal olefin from the dimerized vinylidene olefin to produce an olefin product having a reduced vinylidene olefin content and an increased vinyl olefin content compared to said starting olefin mixture.

13 Claims, No Drawings

OLEFIN PURIFICATION PROCESS

BACKGROUND

This invention relates generally to the purification of vinyl olefins and more particularly to the selective removal of branched chain olefin and especially vinylidene olefin impurities by converting them to oligomers which are easily separated from the vinyl olefins.

Olefin mixtures containing vinyl, vinylidene and internal olefins of similar carbon number are difficult to separate by distillation based solely on the olefin type because vinyl, vinylidene and internal olefins having the same carbon number boil very close together. This is generally the case when the olefins are made by a process capable of producing all three types of olefins. For example, the ethylene chain growth process using triethylaluminum followed by olefin displacement as practiced commercially can produce olefins containing from 4 to up to 30 or more carbon atoms. The olefin product is mainly vinyl olefins, i.e. $R-CH=CH_2$ wherein R is an aliphatic hydrocarbon group, but it also contains lesser amounts of internal olefins, and vinylidene olefins.

In some uses the vinylidene olefin content of olefin mixtures is not detrimental. However, in some uses, the presence of even a few percent of vinylidene olefin decreases the value of the olefin mixture. For example, detergents can be made by reacting olefin mixtures with hydrogen sulfide to add hydrogen sulfide to the double bond forming a mercaptan. These in turn can be oxidized to form sulfonic acids which when converted to their salts are effective detergents. However, vinylidene olefins react with hydrogen sulfide to form tertiary mercaptans which are very difficult to oxidize to sulfonic acids. Thus a need exists for a process for separating vinylidene olefins from a mixture containing vinyl, vinylidene and internal olefins which mixtures cannot be readily separated by distillation. The process also has to remove the vinylidene olefins without converting a substantial amount of vinyl olefins to undesirable side products such as internal olefins.

It has now been discovered that olefin mixtures containing vinyl, vinylidene and internal olefins can be purified by reacting the mixture using a $BF_3$-phosphorus acid catalyst system in a manner so as to preferentially dimerize the vinylidene olefins such that the vinylidene olefin content can be reduced to below detectable levels (less than 0.1 mole percent). The dimerized product is not only easily separated from the product mixture by distillation but the product is a useful synthetic oil such that even when significant amounts of vinylidene olefins must be removed, the purification process is very economical.

SUMMARY OF THE INVENTION

In accordance with this invention there is provided a process for the selective removal of vinylidene olefin from an olefin mixture containing about 1 to 55 mole percent vinylidene olefin, 0 to 20 mole percent internal olefin and the balance vinyl olefin, said processing comprising:
(a) reacting said olefin mixture in the presence of a $BF_3$/phosphorus acid catalyst system so as to selectively dimerize said vinylidene olefin, and
(b) separating said vinyl olefin and internal olefin from the dimerized vinylidene olefin to produce an olefin product having a reduced vinylidene olefin content and an increased vinyl olefin content compared to said starting olefin mixture.

DETAILED DESCRIPTION

The process is especially useful in removing vinylidene olefins from olefin mixtures made by the Ziegler Process of ethylene chain growth on triethylaluminum followed by olefin displacement. Such olefin products contain about 4 to 30 or more carbon atoms depending on reaction conditions. When used to make olefin containing 12 or less carbon atoms the products are predominantly (i.e. over 80 mole percent) linear vinyl olefins and contain lesser amounts of vinylidene and internal olefins. Such olefins are represented by the following formulas:

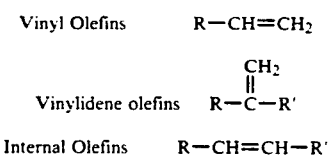

wherein R and R' are alkyl groups.

When the Ziegler Process is used to make higher olefins, the amount of internal and vinylidene olefins increases and also more chain branching occurs. In general, the present process can be used to upgrade an olefin mixture wherein the olefins contain about 6 to 30 carbon atoms of which about 1 to 55 mole percent are vinylidene olefins, about 0 to 20 mole percent are internal olefins and the balance are vinyl olefins. More often the olefin mixtures will contain at least some internal olefins and have the composition of about 1 to 35 mole percent vinylidene, about 0.5 to 12 mole percent internal and the balance, vinyl olefins. The olefin mixture from the chain growth process can be separated into olefin isomers of a single carbon number, such as hexenes or octenes, or a mixture of carbon numbers such as $C_{12}$ to $C_{14}$ or $C_{16}$ to $C_{20}$, for use as olefin feed materials for the process of this invention. In general, vinyl olefins having carbon numbers of about $C_6$ to $C_{30}$ can be purified using the process of this invention. The process is especially effective in obtaining octene-1 products having an octene-1 content of about 98 percent by weight and which contain undetectable levels of vinylidene olefins by NMR analysis. The process rapidly converts the vinylidene olefin to trisubstituted olefin isomers which then are converted to 1:1 dimers with the vinyl olefin. Because an amount of vinyl olefin which is about equal to the amount of vinylidene olefin removed is consumed in forming the dimer, the loss of, for example, a higher and more valuable olefin which is to be purified can be reduced by adding a lower vinyl olefin to the reaction mixture. The second olefin will then co-dimerize with the heavier vinylidenes so as to minimize the lost of the heavier vinyl olefins. The carbon number of the lower olefin is selected based on the boiling point of its dimer so that the small amount of by-product dimer of the lower olefin is not distilled off with the upgraded product.

The catalyst system is $BF_3$ and a phosphorus acid, for example, phosphoric or phosphorous acid and the like. Commercially available phosphoric acid which contains about 85 weight percent $H_3PO_4$ and 15 weight percent water to reduce its viscosity for more convenient handling can be used as well as other compositions with more or less water, e.g. from about 5 to 50 weight percent. Suitable catalysts contain at least about 30 weight percent $BF_3$ and preferably about 40 to 53 weight percent $BF_3$ and from about 47 to 70 weight percent of 85 percent $H_3PO_4$. Catalysts containing about 45 weight percent $BF_3$ and 55 weight percent of $H_3PO_4$ are most preferred for octene purification at good reaction rates while minimizing side reactions. Using $H_3PO_4$ alone (2 weight percent) gives no reaction with octenes. Using 4 weight percent of $BF_3$ catalyst promoted by water and/or water plus ethylene glycol with no $H_3PO_4$ results in moderate isomerization but gives no dimer.

The amount of catalyst affects the rate of reaction. Amounts of catalyst of from about 0.5 to 7 weight percent (combined weight of $BF_3$ and phosphorus acid based on the weight of olefin mixture can be used with amounts of about 0.8 to 4 weight percent being preferred to provide reaction times of about 15 to 30 minutes.

The reaction temperature also effects the rate of reaction and suitable temperatures generally range from about $-15°$ to $60°$ C. The amount of catalyst and the reaction temperature can be selected to provide the desired reaction time for any particular process. Higher temperatures and catalyst concentrations also increase isomerization of the vinyl olefins so that combinations of relatively high catalyst concentration and temperature which cause substantial isomerization of vinyl olefins should be avoided. Preferred reaction conditions for the dimerization are low temperatures (about $5°$ C. to $20°$ C.) and low catalyst concentrations (0.8 to 4 weight percent). As discussed below, a high rate of agitation of the reaction mixture is used to achieve rapid dimerization of the vinylidene olefins.

It has been found to be important to thoroughly disperse the catalyst in the reaction mixture such that the vinylidene olefin dimerization reaction is completed in a reasonable time when using temperatures and catalyst concentrations which minimize side reactions. It is desirable to keep any increase in the amount of internal olefins to less than about 75 percent of the original amount and more preferably less than 50 percent. Larger amounts of internal olefins generally occur with heavier carbon number product (about 1 to 3%) while the increase with lighter olefins can be kept to less than about 0.2 mole percent.

The reaction mixture is agitated to accomplish the dispersion of the catalyst. Other mixing means can be employed including, for example, reactors equipped with static or sonic mixing devices which are effective to disperse the catalyst and promote the rapid dimerization of the vinylidene olefins with the vinyl olefins.

After the dimerization reaction has been completed, the vinyl and internal olefins are separated from the dimerized vinylidene olefins by distillation using an inert atmosphere such as nitrogen.

The invention is further illustrated by, but is not intended to be limited to, the following examples.

Examples 1-7 were carried out in a glass autoclave equipped with a motor driven blade-type impeller, magnetic stirrer, circulating water bath temperature control system, nitrogen purge, catalyst injection port and venting ports from which samples were taken for analysis during the process. A counter-rotating magnetic stirrer was used to supplement the mechanical agitator and eliminate any dead space at the bottom of the autoclave as the height of the mechanical stirrer was not adjustable.

The process of the examples was carried out using the following general procedure while varying the catalyst concentration and proportions, the temperature, and the stirring rate. A 150 gram (1.34 mmole) portion of octene mixture, which contained, by weight percent, 96.46 percent 1-octene, 2.0 percent $C_8$ vinylidene, 1.04 percent $C_8$ linear internal, 0.11 percent $C_8$ branched deep internal, and 0.39 percent paraffins, was weighed into the nitrogen purged autoclave. The cooling bath temperature was established during the nitrogen purge. The autoclave was then sealed under a slight nitrogen pressure of about 3 psig. The catalysts were prepared by combining various proportions of $BF_3$ and 85 percent $H_3PO_4$ and weighing the resulting mixtures into a nitrogen purged syringe. A needle was inserted into the catalyst injection port and the nitrogen pressure in the autoclave was allowed to purge the needle. The syringe was connected to the needle and the needle tip lowered into the octene. The catalyst was added in one portion and the reaction time was measured from the time of catalyst addition. The reaction was monitored by removing and quenching portions of the reaction mixture in 10 weight percent aqueous NaOH at five minute intervals for 30 minutes and then at 10 minute intervals up to one hour total reaction time. The samples were analyzed by gas chromatography (G. C.) to determine vinyl content, vinylidene depletion, trisubstituted olefin appearance/subsequent depletion, dimer formation and by-product formation.

EXAMPLES 1-4

A series of reactions were carried out according to the above procedure using to 40/60 weight percent $BF_3/H_3PO_4$ catalyst ratio at an impeller speed of 1500 rpm, temperatures of $17°$ C. and $30°$ C. and catalyst concentrations of 2 and 4 weight percent of olefin mixture. The reaction conditions and results are reported in Table I.

TABLE I

| Example | Wt. % Catalyst | Temp. | Time[1] | Area % Int.[2] | Area % Tri[4] |
|---|---|---|---|---|---|
| 1 | 2 | 17° C. | 30 | 1.45 | 0.18 |
| 2 | 2 | 30° C. | 20[3] | 1.95 | 0.31 |
| 3 | 4 | 17° C. | 25 | 2.00 | 0.10 |
| 4 | 4 | 30° C. | 15 | 2.58 | 0.14 |

[1]Minutes for removal of vinylidene olefin
[2]Internal olefin at Time
[3]High residual trisubstituted olefins
[4]Trisubstituted olefins at Time The process of Examples 1-4 was repeated using an impeller speed of only 750 rpm in order to illustrate the need for good mixing. The results are shown in Table II.

TABLE II

| Comparison | Wt. % Catalyst | Temp. | Time[1] | Area % Int.[2] | Area % Tri[3] |
|---|---|---|---|---|---|
| 1 | 2 | 17° C. | 60+ | 1.47 | 0.18 |
| 2 | 2 | 30° C. | 60+ | 1.29 | 0.72 |
| 3 | 4 | 17° C. | 40 | 1.60 | 0.11 |
| 4 | 4 | 30° C. | 40 | 2.70 | 0.14 |

[1]Minutes for removal of vinylidene olefin
[2]Internal olefin at Time
[3]Trisubstituted olefin at Time The product analysis for Example 1, Table I, compared to the olefin feed is as follows in weight percent.

|  | Feed | Product |
|---|---|---|
| 1-Octene | 96.46 | 97.86 |
| Vinylidene | 2.00 | 0.00 |
| Tri-Sub. | 0.00 | 0.18 |
| Linear Internal | 1.04 | 1.45 |
| Branched Deep Internal | 0.11 | 0.10 |
| Paraffins | 0.39 | 0.41 |

The results of Examples 1–4, as reported in Table I where the process was completed in 30 minutes or less, demonstrate that effective agitation is necessary for the rapid removal of vinylidene olefins and that lower temperatures and catalyst concentrations are preferred to minimize isomerization. No vinylidene olefins were detected by NMR (less than 0.1 percent). Also, the results in Example 2 and Comparison 2 indicate that higher temperatures tend to decrease catalytic activity.

EXAMPLES 5–6

The general procedure was followed using a 45/55 weight percent $BF_3/H_3PO_4$ catalyst ratio at an impeller speed of 1500 rpm, a catalyst concentration of 2 weight percent and temperatures of 10° and 17° C. The results are reported in Table III.

TABLE III

| Example | Wt. % Catalyst | Temp. | Time[1] | Area % Internal Olefin[2] |
|---|---|---|---|---|
| 5 | 2 | 10° C. | 20 | 0.99 |
|  |  |  | 25[3] | 1.45 |
| 6 | 2 | 17° C. | 15 | 1.45 |
|  |  |  | 20[3] | 1.63 |

[1] Minutes for removal of vinylidene olefin
[2] At Time
[3] Time to disappearance of trisubstituted olefins The results in Table III show that a catalyst composition containing 45 weight percent $BF_3$ provided rapid conversion of vinylidene olefins even at 10° C. while minimizing the increase in internal olefins.

When the general procedure was repeated at an agitation rate of 1500 rpm using 4 weight percent catalyst containing a 25/70 weight percent $BF_3/H_3PO_4$ at either 30° C. and 50° C. the reaction was not complete after 60 minutes with high remaining amounts of trisubstituted olefins (0.35 and 0.62 area percent respectively). Using 1 weight percent catalyst containing 45/55 weight percent $BF_3/H_3PO_4$ at 12° C. also gave an incomplete reaction after 60 minutes. A process using 4 weight percent of a $BF_3/2H_2O$ catalyst gave little reaction at 17° C. after 60 minutes. A process using 4 weight percent of a $BF_3.2H_2O$/polyethylene glycol catalyst at 30° C. also provided little reaction after 60 minutes.

EXAMPLE 7

The general procedure was used to treat an olefin mixture containing by weight percent, 96.8 percent 1-octene, 1.8 percent vinylidene, 0.9 percent linear internal, 0.2 percent branched deep internal, and 0.3 percent paraffins using an impeller speed of 1500 rpm and 1 weight percent of 45/55 weight percent $BF_3/H_3PO_4$ catalyst at 10° C. The vinylidene removal was complete at about 30 minutes with an increase in internal olefins of only about 0.16 area percent in the gas chromatograph (from about 0.90 up to about 1.06 area percent). The octene-1 was separated from the dimer by distillation in a nitrogen purged distillation apparatus using a 4-inch Vigreux Column and a water cooled condenser. The product was collected in a flask cooled by a dry ice/acetone bath (−78° C.). The pot temperature was about 122° C. with overhead temperatures ranging from about 110°–115° C. The distillate was collected in two cuts. The G. C. analysis for the starting product, the distillate cuts and the bottoms are as follows:

| Material | G. C. Area % | | | |
|---|---|---|---|---|
|  | Product | Cut 1 | Cut 2 | Bottoms |
| Octene-1 | 95.74 | 98.44 | 97.67 | 62.66 |
| Internal | 1.06 | 1.03 | 1.46 | 1.21 |
| Tri-Sub | 0.10 | 0.09 | 0.11 | 0.09 |
| Dienes | 0.00 | 0.00 | 0.00 | 0.03 |
| C-9-C= | 0.04 | 0.02 | 0.07 | 0.13 |
| Decene-1 | 0.06 | 0.02 | 0.05 | 0.53 |
| C-8 ROH | 0.21 | 0.05 | 0.21 | 3.15 |
| C16 Dimer | 2.41 | 0.00 | 0.00 | 30.15 |
| Trimer | 0.00 | 0.00 | 0.00 | 1.18 |
| Octane | 0.25 | 0.24 | 0.34 | 0.28 |
| Unknown | 0.13 | 0.11 | 0.09 | 0.59 |
| Total Wt. Grams | 30.16 | 26.26 | 0.96 | 2.19 |

EXAMPLES 8–10

Catalyst for the co-dimerization reactions of Examples 8–10 was prepared in a 5 gallon stainless steel jacketed vessel equipped with an agitator. Two gallons of 85% $H_3PO_4$ was loaded into the reactor and $BF_3$ was then sparged into the $H_3PO_4$ until it was saturated. Agitation was maintained during saturation and brine was supplied to the jacket to maintain constant temperature. For the co-dimerization reactions, 120 pounds each of light olefin and heavy olefin were loaded into a glass lined reactor. In Example 8 $C_{14}$ olefin was upgraded with $C_6$ olefin. In Example 9 $C_{12}$ olefin was upgraded with $C_8$ olefin and in Example 10 $C_{16}$ olefin was upgraded with $C_{10}$ olefin. The reaction mass was cooled to 10° C. and then the catalyst was added. The amount of catalyst used in each run is given in Tables IV–VI. The reaction typically had a heat kick of 10° C. in the first 15 minutes, after which the temperature could be controlled to about 15° C. with brine in the jacket. Upon completion of the co-dimerization reaction, the reaction mass was transferred to a 100 gallon wash pot that had been previous loaded with 9 gallons of water and one gallon of 25 percent NaOH. The crude product was agitated for 5 minutes and the allowed to settle for 20–30 minutes. The initial caustic wash was then followed by two water washes. Washing and settling was done at 50° C. to give a better phase separation. The crude product was distilled to recover the upgraded products. The approximate compositions of the feed olefins was as follows:

| Carbon No. | Feed Olefin Isomer Dist. By NMR | | | |
|---|---|---|---|---|
|  | Vinyl | Int | VD | Tri |
| C6 | 98.3 | 0.4 | 1.4 | ND |
| C8 | 97.4 | 0.6 | 2.1 | ND |
| C10 | 95.1 | 1.2 | 3.7 | ND |
| C12 | 93.6 | 1.2 | 5.2 | ND |
| C14 | 85.3 | 3.2 | 11.5 | ND |
| C16 | 81.7 | 4.7 | 13.5 | ND |

ND = None detected

The reaction times, catalyst concentrations, product yields, and product analysis are shown in Tables IV, V, and VI.

TABLE IV

$C_6$-$C_{14}$ Co-Dimerization Runs

| Run No | Wt. % Catalyst | Rx Time. Hrs | $C_6$ Product Isomer Dist. by Cap GC | | | | $C_{14}$ Product Isomer Dist. by Cap GC | | | | Recovery of Linear[1] $C_{14}$ Olefin, Wt % |
|---|---|---|---|---|---|---|---|---|---|---|---|
| | | | Vinyl | Int[2] | Vd[3] | Tri[4] | Vinyl | Int | Vd | Tri | |
| 8-1 | 0.83 | 3.00 | 100.00 | — | — | — | 95.15 | 4.16 | — | 0.70 | 65 |
| 8-2 | 0.83 | 3.00 | 100.00 | — | — | — | 94.78 | 4.46 | — | 0.76 | 77 |
| 8-3 | 0.92 | 3.00 | 100.00 | — | — | — | 95.12 | 4.44 | — | 0.44 | 76 |

[1] Final distilled product
[2] Internal olefin
[3] Vinylidene olefin
[4] Trisubstituted olefin

TABLE V

$C_8$-$C_{12}$ Co-Dimerization Runs

| Run No | Wt. % Catalyst | Rx Time. Hrs | $C_8$ Product Isomer Dist. by Cap GC | | | | $C_{12}$ Product Isomer Dist. by Cap GC | | | | Recovery of Linear[1] $C_{12}$ Olefin, Wt % |
|---|---|---|---|---|---|---|---|---|---|---|---|
| | | | Vinyl | Int[2] | Vd[3] | Tri[4] | Vinyl | Int | Vd | Tri | |
| 9-1 | 0.83 | 1.00 | 95.64 | 4.36 | — | — | 96.22 | 3.70 | — | 0.08 | 62 |
| 9-2 | 0.83 | 0.25 | 96.54 | 2.83 | — | 0.62 | 97.17 | 2.56 | — | 0.27 | 82 |
| 9-3 | 0.83 | 0.28 | 94.04 | 5.12 | — | 0.84 | 95.80 | 3.91 | — | 0.29 | 80 |
| 9-4 | 0.83 | 0.50 | 96.63 | 2.65 | — | 0.72 | 97.28 | 2.42 | — | 0.30 | 73 |

[1] Final distilled product
[2] Internal olefin
[3] Vinylidene olefin
[4] Trisubstituted olefin

TABLE VI

$C_{10}$-$C_{16}$ Co-Dimerization Runs

| Run No | Wt. % Catalyst | Rx Time. Hrs | $C_{10}$ Product Isomer Dist. by Cap GC | | | | $C_{16}$ Product Isomer Dist. by Cap GC | | | | Recovery of Linear[1] $C_{10}$ Olefin, Wt % | Recovery of Linear[1] $C_{16}$ Olefin, Wt % |
|---|---|---|---|---|---|---|---|---|---|---|---|---|
| | | | Vinyl | Int[2] | Vd[3] | Tri[4] | Vinyl | Int | Vd | Tri | | |
| 10-1 | 0.63 | 1.00 | 97.83 | 1.77 | — | 0.40 | 93.77 | 5.67 | — | 0.57 | 67 | 80 |
| 10-2 | 0.58 | 1.00 | 98.07 | 1.51 | — | 0.42 | 92.33 | 4.93 | — | 2.74 | 68 | 87 |
| 10-3 | 0.77 | 1.00 | 97.55 | 2.00 | — | 0.45 | 94.17 | 5.30 | — | 0.53 | 75 | 78 |
| 10-4 | 0.77 | 1.00 | 97.37 | 2.22 | — | 0.40 | 94.05 | 5.45 | — | 0.50 | 71 | 77 |

[1] Final distilled product
[2] Internal olefin
[3] Vinylidene olefin
[4] Trisubstituted olefin

We claim:

1. A process for the selective removal of vinylidene olefin from an olefin mixture containing about 1 to 55 mole percent vinylidene olefin, 0 to 20 mole percent internal olefin and the balance vinyl olefin, said process comprising:
   (a) selectively dimerizing said vinylidene olefin by reacting said olefin mixture in the presence of a $BF_3$/phosphorus acid catalyst system, and
   (b) producing an olefin product having a reduced vinylidene olefin content compared to said starting olefin mixture by separating said vinyl olefin and internal olefin from the dimerized vinylidene olefin.

2. The process according to claim 1 wherein said catalyst contains from about 30 to 53 weight percent $BF_3$ and from about 47 to 70 weight percent of $H_3PO_4$.

3. The process according to claim 1 wherein said catalyst is present in from about 0.5 to 7 weight percent of the olefin mixture.

4. The process according to claim 1 wherein said olefin mixture is reacted at a temperature of from about $-15°$ to $60°$ C.

5. The process according to claim 1 wherein said olefins in said mixture have carbon numbers of about $C_6$ to $C_{30}$, said catalyst contains from about 30 to 53 weight percent $BF_3$ and from about 47 to 70 weight percent of $H_3PO_4$, said catalyst is present in from about 0.5 to 7 weight percent of the olefin mixture and said olefin mixture is reacted at a temperature of from about $-15°$ to $60°$ C.

6. The process according to claim 1 wherein the vinylidene olefin in said olefin product is less than about 0.1 mole percent.

7. The process according to claim 6 wherein any increase in the amount of internal olefins is less than about 75 percent of the original molar amount of internal olefins in said olefin mixture.

8. The process according to claim 1 wherein said olefin mixture is a mixture of octenes.

9. The process according to claim 5 wherein said olefin mixture is a mixture of octenes, said catalyst contains from about 40 to 45 weight percent $BF_3$ and from about 55 to 60 weight percent of $H_3PO_4$, said catalyst is present in from about 0.8 to 4 weight percent of the olefin mixture and said olefin mixture is reacted at a temperature of from about $5°$ to $20°$ C.

10. The process according to claim 9 wherein said $H_3PO_4$ is 85 weight percent aqueous $H_3PO_4$.

11. The process according to claim 1 wherein a lower vinyl olefin is added to said olefin mixture so as to reduce the amount of vinyl olefin in said mixture which is lost by dimerization with the vinylidene olefins in said mixture.

12. The process of claim 11 wherein the carbon number of the lower olefin is selected such that its dimer has a higher boiling point than the olefin product to permit the product to be separated from said dimer by distillation.

13. The process according to claim 1 wherein the acid is phosphoric acid.

* * * * *